United States Patent [19]
Grismer

[11] Patent Number: 5,133,737
[45] Date of Patent: Jul. 28, 1992

[54] SURGICAL GRASPING INSTRUMENT

[76] Inventor: Jerome T. Grismer, 3 Northwest Ct., Little Rock, Ark. 72212

[21] Appl. No.: 742,160

[22] Filed: Aug. 1, 1991

Related U.S. Application Data

[63] Continuation of Ser. No. 502,937, Apr. 2, 1990, abandoned.

[51] Int. Cl.$^5$ .............................................. A61B 17/28
[52] U.S. Cl. .................................. 606/205; 81/427.5
[58] Field of Search ............... 606/174, 175, 205-209, 606/148, 139; 81/427.5, 415; 30/252; 433/159

[56] References Cited

U.S. PATENT DOCUMENTS

| | | | |
|---|---|---|---|
| 2,669,993 | 2/1954 | Curutchet | 606/205 |
| 3,404,683 | 10/1968 | Eizenberg | 606/208 X |
| 3,407,816 | 10/1968 | Curutchet | 606/174 X |
| 4,452,246 | 6/1984 | Bader et al. | 606/174 X |
| 4,600,007 | 7/1986 | Lahodny et al. | 606/174 |
| 4,674,501 | 6/1987 | Greenberg | 606/174 |
| 4,950,273 | 8/1990 | Briggs | 606/205 X |

*Primary Examiner*—Michael H. Thaler
*Attorney, Agent, or Firm*—Hill, Van Santen, Steadman & Simpson

[57] ABSTRACT

A surgical grasping instrument of the type having finger rings and may or may not have a ratchet lock for securing closure and two arms to the jaw joint is provided with enhanced control in the form of a strut or a thin metal bridging platform extending outwardly from at least one arm and to be engaged by either or both the thumb and the third finger of the surgeon during manipulation of the instrument, thereby improving the leverage and hand control of the instrument.

6 Claims, 1 Drawing Sheet

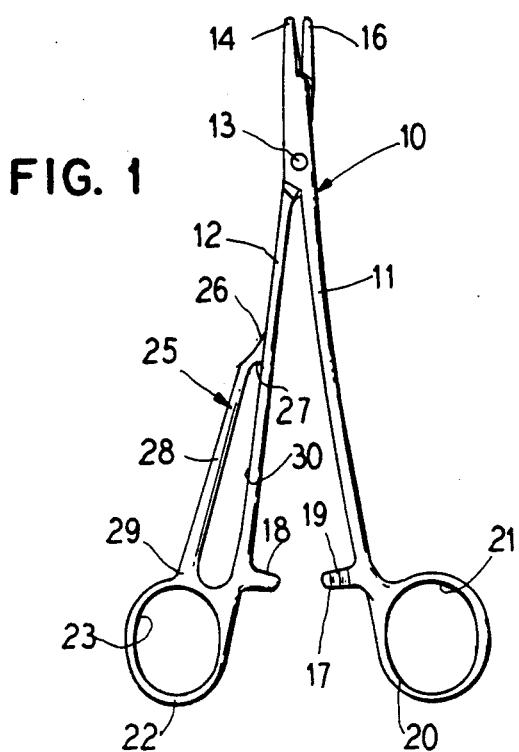
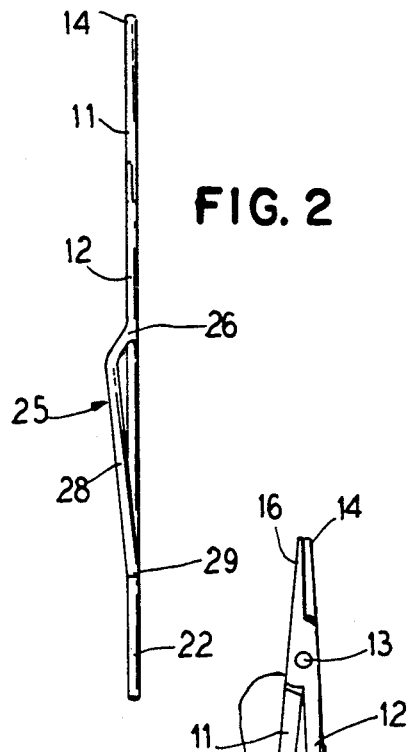

SURGICAL GRASPING INSTRUMENT

This is a continuation of application Ser. No. 07/502,937, filed Apr. 2, 1990 now abandoned.

BACKGROUND OF THE INVENTION

1. Field of the Invention

This invention relates generally to surgical instruments and more particularly to a means for improving the surgeon's hand control in a so-called surgical grasping instrument.

2. Description of the Prior Art

Grasping instruments of the prior art have been provided with trigger loops by means of which the surgeon can engage the loop with the first finger, sometimes referred to colloquially as "the trigger finger" or "index finger" and by so engaging the loop effect some functional purpose associated with the use of the instrument. For example, see the following patents: Vacheresse U.S. Pat. No. 2,748,773 issued Jun. 5, 1956, Wood U.S. Pat. No. 3,169,526 issued Feb. 16, 1965 and Shannon U.S. Pat. No. 3,533,410 issued Oct. 13, 1970.

SUMMARY OF THE INVENTION

A surgical grasping instrument is very often used as a needle holder in the course of carrying out a surgical procedure requiring the placement of sutures or as a grasping instrument on blood vessel or tissue. The manipulation of the grasping instrument requires a great deal of skill and dexterity and it is essential to a successful operation that the surgeon have the grasping instrument used under the greatest amount of control possible.

In accordance with the principles of the present invention, the standard commercially available surgical grasping instrument is modified to improve the surgeon's hand control. More specifically, the standard instrument which has finger rings, may or may not have a rachet mechanism for securing closure and two arms extending to a jaw joint, is provided with a thumb platform. It is contemplated that the platform could be provided by either a strut, or by a planar surface extending laterally from an adjoining arm. With that enhanced abutment surface available for engagement by the thumb of the surgeon, greatly improved manipulative dexterity is achieved since the surgeon enjoys better control of the instrument and can utilize the instrument with improved accuracy and skill.

BRIEF DESCRIPTION OF THE DRAWINGS

FIG. 1 is a full front elevational view of a surgical grasping instrument embodying the principles of the present invention;

FIG. 2 is a side elevational view of the instrument of FIG. 1;

FIG. 3 is a view of the instrument of the present invention in simulated use and illustrating the positioning of the hand and fingers of the surgeon as he manipulates the instrument;

FIG. 4 is a view somewhat similar to FIG. 1 and showing another form of the inventive subject matter in a different embodiment of the invention;

FIG. 5 is a side elevational view of the modified instrument of FIG. 4; and

FIG. 6 is a partial cross-sectional view taken on line VI—VI of FIG. 4.

DESCRIPTION OF THE PREFERRED EMBODIMENTS

While the principles of the present invention find a particular utility in a surgical grasping instrument for holding needles during suturing, it should be appreciated that the inventive subject matter could be incorporated in other forms of surgical instruments wherein the improvements herein contemplated would also find application. Accordingly, the specific instrument herein illustrated and described is one embodiment of the invention as an exemplification of the concept of improving hand control.

In surgical procedures, it is common to use one or the other or two generally accepted techniques. The "finger method" of grasping or holding and handling a surgical instrument such as a grasping instrument locates the distal digit of the thumb in one of the rings and the third finger is located in the other ring. The first finger is positioned to lie adjacent the arms extending towards the jaw joint and the second finger can simply lie adjacent to the external surface of the ring in which the third finger is situated.

The "palm method" of grasping or holding and handling a surgical instrument such as a grasping instrument usually locates the distal end of the third or fourth finger in the ring while the thumb arm ratchet position is controlled by the base of the thumb, (thenar-first metacarpal joint movement). The opposite arm of the instrument is controlled with the fingers. The palm method is a most common grasp utilized by many surgeons.

Referring to the drawings, the surgical grasping instrument of the present invention is shown generally at 10 and comprises a pair of arms identified respectively at 11 and 12 disposed in co-planar relationship and hinged together by a pivot pin 13, thereby to achieve a scissors-like action between an open position and a closed position.

At one end of the arms a vise is formed by a pair of complemental clamps or jaws, there being a vise jaw 14 formed at the end of the arm 11 and a vise jaw 16 formed at the end of the arm 12.

In order to selectively lock the instrument 10 in a closed locking position, there is provided a locking means on the side of the hinge pin 13 opposite the vise jaws 14 and 16. A ratchet locking lug 17 is formed on the arm 11 and extends inwardly towards the other arm 12. A complemental ratchet locking lug 18 is formed on the arm 12 and extends inwardly towards the arm 11. The adjoining surfaces of the locking lugs 17 and 18 are formed with interengaging ratchet teeth 19. The ratchet teeth can be selectively interengaged by moving the instrument towards the closed position, thereby to retain the instrument locked. However, by appropriate handling and movement of the arms 11 and 12 towards an open position, the ratchet teeth 19 can be disengaged and the instrument 10 opened.

To facilitate the handling and manipulation of the instrument, there is provided finger engagement means at the free ends of the arms 11 and 12. A ring 20 is formed at the free end of the arm 11. The ring 20 is generally circular in configuration and extends laterally outwardly in the plane of the instrument, thereby to provide a finger opening shown at 21.

In like manner, a ring 22 is formed on the end of the arm 12 and extends laterally outwardly in the plane of the instrument, thereby to provide a finger opening shown at 23.

In accordance with the principles of the present invention, control improvement means are provided to enhance the leverage the hand control and the stability exercised by the surgeon. Referring to FIGS. 1 and 2, there is provided a strut shown generally at 25 which extends laterally outwardly of the arm 12 at a medial position 26. The strut projects laterally outwardly and is angularly offset out of the plane of the instrument 10, thereby to provide an abutment surface shown at 27. The strut proceeds longitudinally at a reentrant angle as at 28 and is joined to the ring 22 as at 29 at that portion which is projecting laterally outwardly. There is thus provided a thumb platform by means of which the surgeon can stabilize the manipulation of the instrument and gain enhanced hand control and additional leverage. The strut 25 is spaced longitudinally outwardly of the arm 12 by a spacing dimension represented by the opening shown in FIG. 1 at 30. If desired, the space 30 can be closed by a web or thin metal bridge to form a flat engagement surface for engagement by the adjoining surface of the surgeon's thumb.

Referring now more particularly to FIGS. 4, 5 and 6, a slightly modified form of the invention is illustrated wherein there is provided an enhanced control mean for the "ring finger" as well as for the thumb. Many of the parts of the grasping instrument of FIGS. 4, 5 and 6 are identical in shape, location and function and accordingly like parts are identified with like reference numerals.

The control means forming the thumb platform is generally similar to that already described at 25 and subsequent reference numerals. However, in FIG. 4, the strut is shown at 25a and extends outwardly from a medial portion of the arm 12 as at 26a, but in co-planar relation with the remaining parts of the instrument 10. Thus, a longitudinally extending portion 28a joins the ring 22 as at 29a. The space 30a between the strut 28a and the arm 12 is completely filled as, for example, by a thin metal bridge, thereby forming a flat engagement surface 31.

In order to provide control means for the third finger or so-called ring finger, the arm 11 has a strut 35 projecting outwardly therefrom as at a medial portion 36. The strut 35 proceeds longitudinally as at 37 and is joined to an outwardly projecting portion of the ring 20 as at 38. The space between the strut 35 and the arm 11 is closed by a flat member, for example, a thin metal forming a planar engagement surface 39, thereby providing a control platform for the third or ring finger.

Referring now to FIG. 3, the surgical grasping instrument of the present invention is shown in a simulated "palm method" of grasping. The ring 22 is shown positioned over the first metacarpal joint of the thumb shown approximately at 40 and the end of the ring is positioned over the thenar area shown at 41. The distal end of the thumb is shown at 42 and registers conveniently in a nested relationship with the strut 25. The user can exert pressure against the shoulder or abutment surface 27.

By virtue of the improved control means, the surgeon enjoys an improved leverage and stability and better hand control in the manipulation of the instrument 10.

It will be understood that the platforms herein illustrated could be modified within the spirit of this invention in terms of relative length, configuration, etc. in direct response to the size length and arm tension of the instrument and the surgeons individual preference.

Although minor modifications might be suggested by a person of ordinary skill in the art, it should be understood that I wish to embody within the scope of my invention all such modifications as reasonably and properly come within the scope of my contribution to the art.

I claim as my invention:

1. A surgical instrument comprising two co-planar arms medially pivotally hinged together and relatively movable with respect to one another in a scissors-like action between a first open position and a second closed position, complemental pinchers formed at one end of said arms and together with one another forming a vise with selectively openable and closable jaws for grasping and holding objects between said jaws;

finger engaging means at the opposite end of said arms comprising a ring extending outwardly from each respective arm; and control improvement means comprising means forming a thumb platform disposed to extend outwardly from a medial portion of one of said arms and joining the outwardly projecting portion of a corresponding one of said rings;

said control improvement means comprising a strut spaced outwardly of said arm to form an opening between the arm and the strut, said strut being formed and disposed to extend longitudinally at an angle to connect with the outwardly projecting portion of a corresponding ring;

said outwardly spaced strut forming a platform separate from the arm and engageable by either or both the thumb and the third finger of the surgeon during manipulation of the instrument to improve leverage, stability and hand control of the surgical instrument, wherein said strut is in part offset angularly out of the plane of said arms, thereby to form a recess for receiving the thumb of a user and having an abutment shoulder at one end of said recess for engagement by the thumb during use.

2. A surgical instrument comprising two co-planar arms medially pivotally hinged together and relatively movable with respect to one another in a scissors-like action between a first open position and a second closed position, complemental pinchers formed at one end of said arms and together with one another forming a vise with selectively openable and closable jaws for grasping and holding objects between said jaws;

locking means at an opposite end of said arms comprising a toothed ratchet lug on each arm extending inwardly from each respective arm and interengaging with one another to lock the arms in a closed vise gripping position;

finger engaging means at the extreme said opposite end of said arms comprising a ring extending outwardly from each respective arm; and control improvement means comprising means forming a thumb platform disposed to extend outwardly from a medial portion of one of said arms and joining the outwardly projecting portion of a corresponding one of said rings;

said control improvement means comprising a strut disposed to extend outwardly from a medial portion of one arm and offset angularly out of the plane of said arms to form an abutment shoulder and a thumb recess;

said strut being formed to extend longitudinally at a reentrant angle to connect with the outwardly projecting portion of a corresponding ring.

3. A surgical instrument as defined in claim 2 said strut being spaced longitudinally outwardly of said one arm by a spacing dimension closed by a web or thin metal bridge to form a flat engagement surface for engagement by the adjoining surface of the user's thumb.

4. A surgical instrument comprising two co-planar arms medially pivotally hinged together and relatively movable with respect to one another in a scissors-like action between a first open position and a second closed position, complemental pinchers formed at one end of said arms and together with one another forming a vise with selectively openable and closable jaws for grasping and holding objects between said jaws;

finger engaging means at the opposite end of said arms comprising a ring extending outwardly from each respective arm; and control improvement means comprising means forming a thumb platform disposed to extend outwardly from a medial portion of one of said arms and joining the outwardly projecting portion of a corresponding one of said rings;

said control improvement means comprising a strut spaced outwardly of said arm by a spacing dimension closed by a web to form a flat engagement surface, said strut being angularly offset out of the plane of the instrument to provide an abutment surface for the thumb of a user, said strut being formed and disposed to extend longitudinally at an angle to connect with the outwardly projecting portion of a corresponding ring;

said outwardly spaced strut forming a platform separate from the arm and engageable by either or both the thumb and the third finger of the surgeon during manipulation of the instrument to improve leverage, stability and hand control of the surgical instrument.

5. A surgical instrument comprising two co-planar arms medially pivotally hinged together and relatively movable with respect to one another in a scissors-like action between a first open position and a second closed position, complemental pinchers formed at one end of said arms and together with one another forming a vise with selectively openable and closable jaws for grasping and holding objects between said jaws;

finger engaging means at the opposite end of said arms comprising a ring extending outwardly from each respective arm; and control improvement means comprising means forming a thumb platform disposed to extend outwardly from a medial portion of one of said arms and joining the outwardly projecting portion of a corresponding one of said rings;

said control improvement means comprising a strut spaced outwardly of said arm to form a spacing dimension between the arm and the strut closed by a web or thin metal bridge to form a flat engagement surface for engagement by the adjoining surface of the user's thumb, said strut being formed and disposed to extend longitudinally at an angle to connect with the outwardly projecting portion of a corresponding ring;

said outwardly spaced strut forming a platform separate from the arm and engageable by either or both the thumb and the third finger of the surgeon during manipulation of the instrument to improve leverage, stability and hand control of the surgical instrument, wherein said strut is in part offset angularly out of the plane of said arms, thereby to form a recess for receiving the thumb of a user and having an abutment shoulder at one end of said recess for engagement by the thumb during use.

6. A surgical instrument comprising two co-planar arms medially pivotally hinged together and relatively movable with respect to one another in a scissors-like action between a first open position and a second closed position, complemental pinchers formed at one end of said arms and together with one another forming a vise with selectively openable and closable jaws for grasping and holding objects between said jaws;

finger engaging means at an opposite end of said arms comprising a ring extending outwardly from each respective arm; and control improvement means comprising means forming a thumb platform disposed to extend outwardly from a medial portion of one of said arms and joining the outwardly projecting portion of a corresponding one of said rings;

said control improvement means comprising a strut disposed to extend outwardly from a medial portion of one arm and offset angularly out of the plane of said arms to form an abutment shoulder and a thumb recess;

said strut being formed to extend longitudinally at a reentrant angle to connect with the outwardly projecting portion of a corresponding ring;

there being formed between said strut and said one arm a thin metal bridge forming a flat engagement surface for the thumb of a user.

* * * * *